United States Patent [19]

Barger et al.

[11] E Re. 28,657

[45] Reissued Dec. 23, 1975

[54] CRYOSURGICAL APPARATUS

[75] Inventors: J. P. Barger, Winchester; William H. Crandell, Lexington; Thomas W. Gardner, Dearborn Heights, all of Mich.

[73] Assignee: Dynatech Corporation, Burlington, Mass.

[22] Filed: July 12, 1974

[21] Appl. No.: 487,880

Related U.S. Patent Documents

Reissue of:

[64] Patent No.: 3,782,386
Issued: Jan. 1, 1974
Appl. No.: 251,433
Filed: May 8, 1972

[52] U.S. Cl. ..... 128/303.1; 62/293
[51] Int. Cl.[2] ..... A61B 17/36
[58] Field of Search ..... 62/278, 293; 128/303.1

[56] References Cited

UNITED STATES PATENTS

| | | | |
|---|---|---|---|
| 3,398,738 | 8/1968 | Lamb et al. | 128/303.1 |
| 3,434,477 | 3/1969 | Thomas, Jr. | 128/303.1 |
| 3,439,680 | 4/1969 | Thomas, Jr. | 128/303.1 |
| 3,502,081 | 3/1970 | Amoils | 128/303.1 |
| 3,507,283 | 4/1970 | Thomas, Jr. | 128/303.1 |
| 3,536,075 | 10/1970 | Thomas, Jr. | 128/303.1 |
| 3,613,689 | 10/1971 | Crump | 128/303.1 |

FOREIGN PATENTS OR APPLICATIONS

| | | | |
|---|---|---|---|
| 1,552,671 | 11/1968 | France | 128/303.1 |

*Primary Examiner*—Channing L. Pace
*Attorney, Agent, or Firm*—Cesari and McKenna

[57] ABSTRACT

Cryosurical apparatus feeds liquid refrigerant to the hollow tip of a cryosurgical probe through a first conduit to freeze the tip, the refrigerant exhausting from the tip through a second conduit. To defrost the tip, refrigerant in the second conduit is heated and then backflushed through the tip so that it exhausts therefrom through the first conduit. To maintain proper fluid flow through the probe during the defrost mode of operation, the probe contains a third conduit which bleeds fluid from the tip during both modes of operation.

22 Claims, 2 Drawing Figures

CRYOSURGICAL APPARATUS

Matter enclosed in heavy brackets [ ] appears in the original patent but forms no part of this reissue specification; matter printed in italics indicates the additions made by reissue.

BACKGROUND OF THE INVENTION

This invention relates to cryosurgical apparatus. It relates more particularly to an improved cryosurgical probe and control unit therefor.

Generally, cryosurgical apparatus is comprised of a refrigerated probe having a handle and tip. A refrigerant is circulated through the probe tip which brings the tip to a very low temperature. By manipulating the probe, a doctor can effect the precise, localized freezing of body tissue. There is usually provision also for defrosting the probe tip so that the tip can be separated from the tissue without damage to the tissue.

Using the probe, a surgeon can freeze tissue enough to cause the tissue to adhere to the probe tip. This enables the surgeon to manipulate the adhered tissue with reduced probability of tearing. This procedure has, in fact been highly successful in such areas as cataract removal. Tissue cells can also be completely destroyed by lowering the temperature below a certain level using the probe. Cell destruction is involved, for example, in the treatment of cervical erosion.

A number of probe designs have been proposed in the past. However, most are disadvantaged in one respect or another. Some proposed probes are quite complex, requiring heaters, temperature sensors or valves inside the probe. This not only makes the units costly, but it also increases the chances of malfunction in the operating room. Some of the simpler and less expensive probe versions do not maintain close enough control over the probe tip temperatures in both the freeze and defrost modes of operation. Still other units require a relatively long time to cycle between their temperature extremes.

SUMMARY OF THE INVENTION

Accordingly, it is an object of the present invention to provide cryosurgical apparatus which is simple and easy to operate.

Another object of the invention is to provide cryosurgical apparatus which is reliable and safe to use in the operating room.

Yet another object of the invention is to provide cyrosurgical apparatus whose probe tip can be brought to operating temperature and be defrosted relatively quickly.

Yet another object of the invention is to provide cryosurgical apparatus which is relatively inexpensive to make and maintain.

Other objects will in part be obvious and will in part appear hereinafter.

The invention accordingly comprises the features of construction, combination of elements and arrangement of parts which will be exemplified in the construction hereinafter set forth, and the scope of the invention will be indicated in the claims.

The present apparatus is comprised of a console and separate probes. A liquid refrigerant such as nitrous oxide ($N_2O$) from a separate pressurized source is conducted to the console via a flexible or rigid hose. This refrigerant is then circulated in a controlled fashion through the probe which is connected to the console by a second hose in a manner to be described presently.

A typical console described herein contains a pair of three-way solenoid valves which are connected to control the flow of refrigerant. However, combinations of two and three way solenoid valves can be used depending on the flow arrangement. One valve is open during the freeze mode of operation; the other during the defrost mode. Both valves are controlled by a foot switch.

The "freeze" valve is connected by way of a special gas relief valve to be described later in detail to one fluid path leading to the probe. The "defrost" valve is connected by way of a heat exchanger to the other fluid path in the probe hose. The temperature of this heat exchanger is maintained substantially constant by a thermostatically controlled heater.

The probe contains three separate lines to its tip. More particularly, there is a small diameter tube connected from the freeze valve and a larger diameter tube connected from the defrost valve. The third line consists of a small diameter tube which vents to the atmosphere through a third fluid path in the probe hose.

The operator initiates the freeze mode of operation by depressing the foot switch. This opens the freeze valve allowing liquid refrigerant to flow through the small diameter feed tube to the probe tip. The liquid vaporizes at that point, thereby cooling the working surface of the probe tip. The vapor (gas) then exhausts from the probe along two separate avenues.

Most of the gas flows out of the probe tip through the relatively large diameter tube leading to the three way defrost valve where it vents to the atmosphere. In so doing, the escaping gas passes through the heat exchanger which is maintained at a nominal temperature, e.g., 50°C. Thus, when the gas reaches the atmosphere, it is not uncomfortably cold. A smaller portion of the gas leaves the probe through the third tube whereupon it is also vented to the atmosphere. It is not critical to the freeze performance whether or not the exhaust gas passes through the third tube.

As long as the foot switch is depressed, refrigerant will be circulated to the probe to maintain the tip at a very low temperature, on the order of −88°C. This temperature is low enough to freeze the tissue contacted by the tip, causing it to adhere to the tip. Also, prolonged contact by the cold probe tip will actually destroy the tissue.

To defrost the probe tip, the operator releases the footswitch. This causes the freeze valve to close and the defrost valve to open so that refrigerant is now routed to the probe via the heat exchanger. Upon passing through the heat exchanger, the liquid refrigerant is heated, e.g., to +50°C. The warm nitrous oxide is conducted through the relatively large diameter tube to the probe tip where it heats the tip surface and the adhered tissue.

The pressurized fluid flows from the tip through the tube leading to the freeze valve where it exhausts into the atmosphere. It also escapes through the third tube which also vents to the atmosphere.

The three-tube probe construction enables a relatively large volume of heated refrigerant to be rapidly circulated to the probe tip so that the tip is heated in a minimum amount of time.

An adjustable timer in the console controls the duration of the defrost cycle so that the refrigerant supply to the probe is cut off after a selected period of time which is sufficient to thaw the particular tissue contacted by the probe tip. By alternately depressing and releasing the switch, the operator can cycle the probe between its two temperature extremes, thereby alternately freezing and thawing the tissue being operated on.

It is important to appreciate that there are no electrical connections to the probe itself. This not only minimizes maintenance problems, it also eliminates the possibility of a spark produced in the probe igniting very flammable anesthesia vapors near the patient and eliminates electrical hazards to the patient, such as stray leakage current. Also, because the probe tip is completely isolated electrically, it cannot form a path for any spuriously generated electrical inputs on the patient's body from other sources having nothing to do with the cryosurgical treatment. Yet, with all of these advantages, the present apparatus is simple and inexpensive to make, maintain and operate.

DESCRIPTION OF THE PREFERRED EMBODIMENTS

Figure 1:
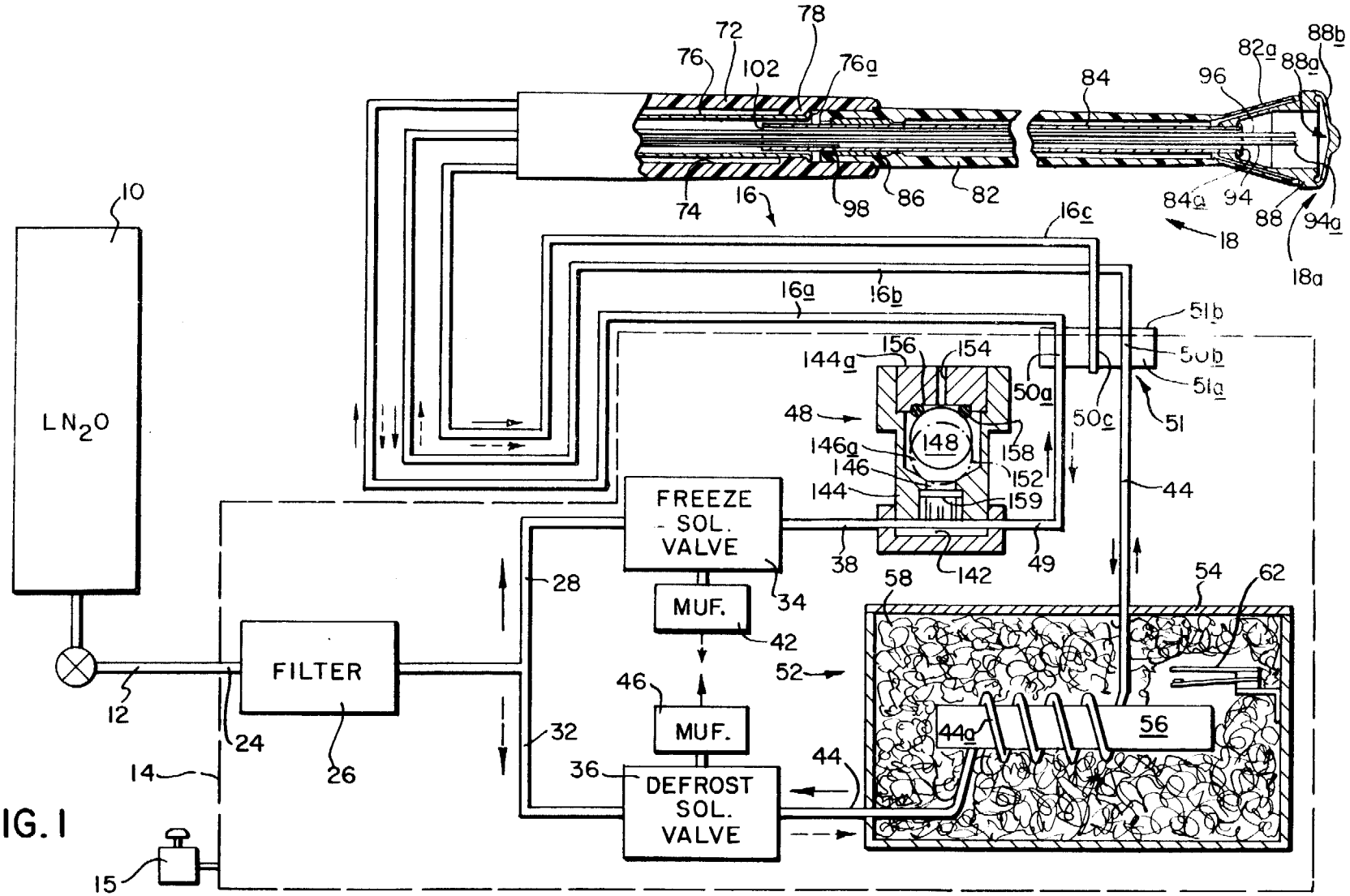
FIG. 1 is a diagrammatic view with parts cut away showing the cryosurgical apparatus embodying the principles of this invention.

Turning now to FIG. 1 of the drawings, a tank 10 filled with liquid refrigerant [nitrous oxide ($N_2O$)] is connected by a valved conduit 12, e.g., a flexible hose, to the cryosurgical apparatus console shown in dotted lines at 14. Apparatus in console 14 is activated by a foot switch 15 to control the further flow of the refrigerant through a flexible hose 16 to a cryosurgical probe shown generally at 18. As the present system uses a liquid refrigerant, the tank 10 is inverted to assure that only liquid is conducted to the console. In place of an inverted tank, a syphon tank may be used.

Conduit 12 actually connects to a pipe 24 inside console 14 which includes a filter 26 designed to remove any particulate material carried by the refrigerant. Pipe 24 then branches into two separate pipes, 28 and 32. Pipe 28 leads to a three-way solenoid valve 34 while line 32 connects with a similar valve 36.

Valve 34 has three ports. One part is connected to pipe 28, the second port is connected to a pipe 38 and the third port vents to the atmosphere through a small muffler 42. Valve 34 has two positions which it assumes when alternately the apparatus is operating either in its freeze or defrost modes. During the freeze mode, the valve opens to conduct fluid from line 28 to pipe 38. During the defrost mode, valve 34 discharges exhaust from pipe 38 through muffler 42 to atmosphere.

Valve 36 operates in much the same way except that its operation is 180° out of phase with that of valve 34. During the freeze mode, valve 36 is arranged to discharge fluid from pipe 44 through the muffler 46 to the atmosphere, while during the defrost mode, the valve opens to conduct fluid from line 32 to a pipe 44. Both valves are actuated by the footswitch 15.

Pipe 38 leads to a special gas relief valve 48 whose operation will be described later. Another pipe 49 connects the valve 48 to one port 50a in the female member 51a of a three-port, quick-disconnect type fluid coupling 51, the member 51a being mounted in the wall of the console 14. The pipe 44 from valve 36, on the other hand, leads to a heat exchanger shown generally at 52.

Heat exchanger 52 consists of a housing 54 containing a heater 56 shown herein as a rod type resistance heating element. The portion 44a of pipe 44 inside housing 54 is tightly wrapped around heater 56 so that it is in intimate heat exchange relation therewith. After leaving the housing, pipe 44 terminates at the port 50b of coupling member 51a. Preferably, housing 54 is filled with a suitable insulation material 58 to reduce heat loss and minimize the size of the heater. The heater 52 is maintained at a selected constant temperature by means of an adjustable heat responsive switch 62 in circuit with the electrical leads to the heater. In a typical application, heater 56 is set at a temperature of about 50°C.

The flexible hose 16 leading to probe 18 is connected to the male coupling member 51b. Hose 16, like coupling 51, has three separate fluid passages 16a, 16b and 16c. These passages are shown as widely separated for ease of illustration only. One hose passage 16a communicates with coupling port 50a; a second passage 16b leads to coupling port 50b and the third passage 16c leads to port 50c which is vented to the atmosphere at the female coupling member 51a inside console 14.

Still referring to FIG. 1, probe 18 has a handle 72. The handle is bored at 74 to accommodate three fluid lines extending between the hose 16 and the tip 18a of probe 18. A metal sleeve 76 somewhat smaller in diameter than bore 74 extends from the rear of the bore inside the handle 72 to an annular restriction 78 near the front of the bore. The sleeve end 76a is flanged and cemented to restriction 78 to help retain the sleeve.

A generally cylindrical plastic barrel extension 82 is received in the front end of bore 74 ahead of restriction 78. The extension contains a stainless steel sleeve 84 whose outside diameter is somewhat less than the inside diameter of sleeve 76. The sleeve extends from a point inside sleeve 76 behind restriction 78 to the probe tip 18a. It is held in place inside barrel 72a by bushing 86 pressed between the outside of sleeve 84 and the inside of extension 82.

The illustrated probe embodiment is used for gynecological surgical procedures. Accordingly, its tip 18a is composed of a relatively large, generally frustoconical metal enclosure 88. Sleeve 84 extends through the smaller end wall of the enclosure 88 and the sleeve end 84a is rolled out against the enclosure wall to provide a firm connection between the two. It should be mentioned also that the forward end of barrel extension 82 is flared at 82a to conform to the contour of the conical enclosure 88. The larger thin front wall 88b of the enclosure constitutes the working surface of the probe.

Probe 18 contains three separate fluid-carrying tubes, 94, 96, and 98. These three tubes extend through a plug 102 inserted into the rear end of sleeve 84 so that they are positioned in spaced-apart relation within the sleeve. Tube 94 has a relatively small internal diameter, i.e., No. 21 AWG stainless steel tubing. This tube extends from a point near the middle of enclosure 88 through sleeves 84 and 76 where it connects with the fluid passage 16a in hose 16. Tube 94 is used as the feed line for liquid refrigerant during the probe's freeze mode of operation and as an exhaust line during the defrost mode.

Tube 96 has a larger diameter, consisting of No. 14 AWG stainless steel tubing. This tube also extends from the middle of enclosure 88 into the probe handle 72 where it connects with the fluid passage 16b of hose 16.

The third tube 98 extends from a point inside sleeve 84 back through sleeve 76 and into the probe handle where it connects with the fluid passage 16c of hose 16. Tube 98 is slightly smaller in diameter than tube 94, i.e., No. 24 AWG stainless steel tubing. The tube 98 functions as a separate vent line for the fluid in the probe during both the freeze and defrost modes of operation. In the defrost mode this enables the probe to reach its temperature extreme very quickly, as will be described later.

Figure 2:
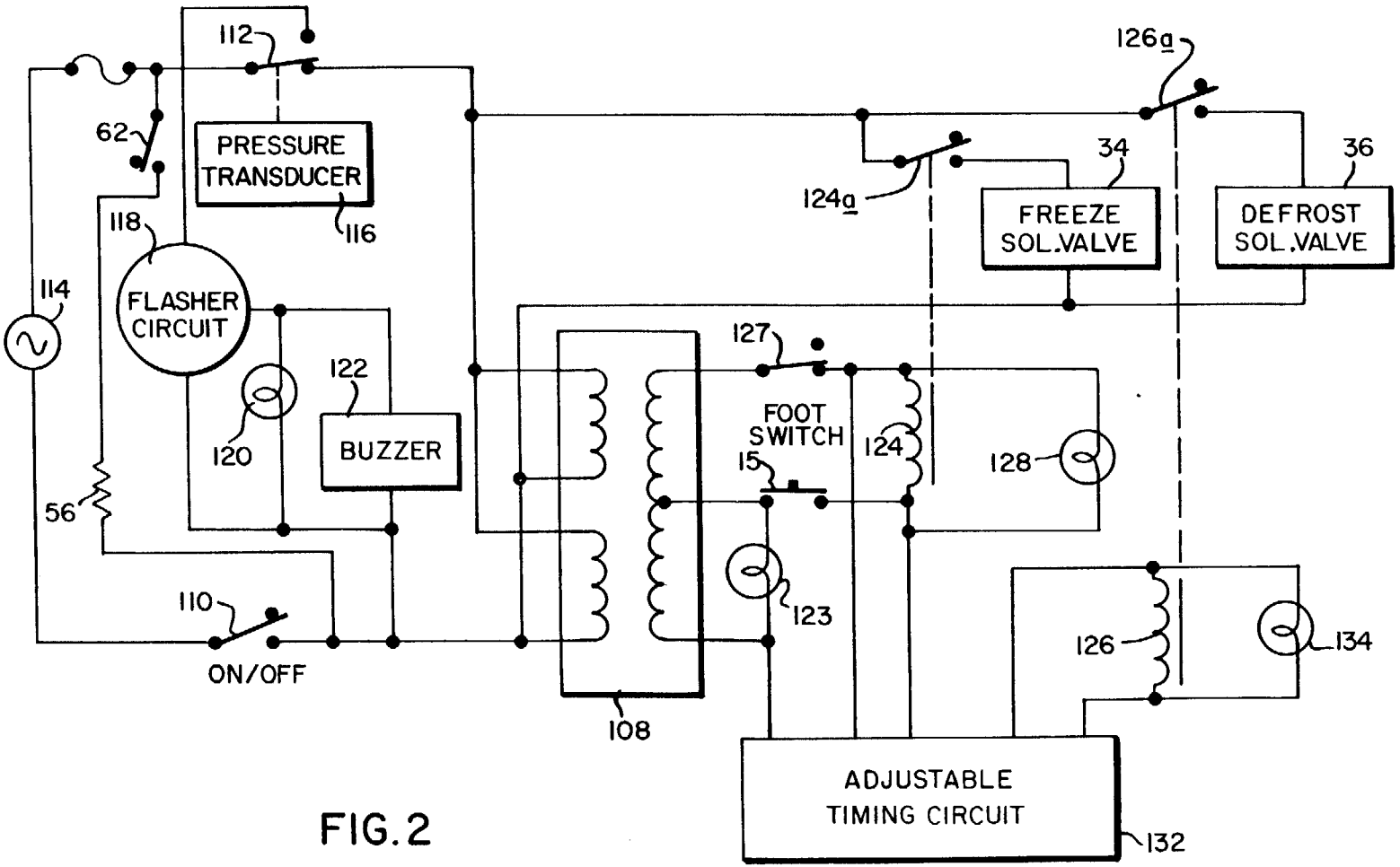
FIG. 2 is a schematic diagram illustrating in greater detail the electrical components of the subject apparatus.

Turning now to FIG. 2 which shows the unit's electrical components inside console 14, the two parallel primary windings of a transformer 108 are connected in a series circuit including an ON/OFF switch 110, a switch 112 and a power source 114. The transformer is energized when the switch 110 is closed unless switch 112 is open. Switch 112 is controlled by a pressure transducer 116 which is exposed to the pressure of the refrigerant in tank 10 (FIG. 1). When the pressure in tank 10 is below a selected value considered insufficient to maintain the proper flow of refrigerant to the probe 18, the transducer 116 will respond to that condition by opening switch 112 so that the apparatus cannot be used.

This low pressure condition also sounds an alarm to warn the operator. More particularly, when switch 112 opens, it completes a series circuit consisting of source 114, a flasher circuit 118, a WARNING panel light 120 and a buzzer 122. The buzzer and light will remain energized until the operator opens switch 110 or increases the refrigerant pressure in the tank.

When the transformer 108 is energized, the system is ready to use. The operator is apprised of this by the illumination of a READY light 123 connected across the lower segment of the secondary winding of transformer 108 and mounted in the front of console 14 (FIG. 1).

A series circuit consisting of heater 56 and its heat responsive switch 62 are connected across the supply voltage source. Heater 56 is energized at the same time as transformer 108 and is controlled at its set point by heat responsive switch 62. Connected across the primary also is a second parallel circuit consisting of a relay contact 124a and valve 34 in one branch and a relay contact 126a and valve 36 in the other branch. Relay contact 124a is normally open. It is closed by energizing an associated relay coil 124. Similarly, contact 126a is normally open and is closed by energizing a relay coil 126.

When relay coils 124 and 126 are deenergized, valves 34 and 36 isolate the refrigerant supply. When coil 124 is energized, solenoid valve 34 is actuated to pass refrigerant from line 28 to line 38 (FIG. 1). At this point, valve 36 is arranged to vent line 44 to the atmosphere through muffler 46 (FIG. 1). When relay coil 126 is energized, valve 36 is actuated so that it conducts refrigerant from line 32 to line 44. At this time, the valve 34 is set to vent line 38 to the atmosphere through muffler 42.

Relay coil 124 is connected in series with foot switch 15 and a microswitch 127 across the upper segment of the secondary winding of transformer 108. Switch 127 is closed only when the coupling members 51a and 51b (FIG. 1) are connected properly. This is a safety feature in that, if the coupling member 51b is not in place, relay 124 cannot be energized to start the refrigerant flow even though foot switch 15 is depressed. Assuming switch 127 is closed, when the foot switch 15 is depressed, the coil 124 is energized. Also, a FREEZE panel light 128 connected across coil 124 is illuminated to apprise the operator that the unit is operating in the freeze mode.

A timing circuit 132 is also connected across the secondary winding of transformer 108 and receives power from the transformer. Circuit 132 is a conventional resistance capacitance electronic circuit having a selected time constant. Preferably also, the circuit includes provision for varying the time constant to suit a particular application. The output of circuit 132 is applied to a parallel circuit consisting of relay coil 126 and a DEFROST panel light 134. When foot switch 15 is released, coil 124 is deenergized, while circuit 132 energizes relay coil 126 and light 134. The apparatus is now in the defrost mode with contact 126a closed and contact 124a open. This situation prevails for a time interval determined by the time constant of circuit 132. After a given time following the release of the foot switch 15, circuit 132 automatically turns off relay 126 and light 134 completing a freeze-thaw operating cycle. The apparatus now reverts to its ready condition until the operator again depresses the foot switch 15.

Turning again to FIG. 1, when the foot switch 15 is depressed and the unit is operating in its freeze mode, the path of refrigerant flow is indicated by the solid line arrows in FIG. 1. Liquid refrigerant flows through valve 34 and thence to probe 18. If there is any residual gas in valve 34 or pipe 38 due to prior operation of the apparatus, this escapes through relief valve 48.

The purpose of valve 48 is thus somewhat similar to that of a steam trap. More particularly, it is designed to vent gas but not liquid from pipe 38 so that the warmer gas does not reach probe 18. The pressurized fluid in pipe 38 is conducted into a horizontal passage 142 at the lower end of the valve housing 144. This passage leads to pipe 49.

Passage 142 also communicates with a vertical chamber 146 extending to the upper end of the housing. The upper portion 146a of chamber 146 is enlarged to accommodate a ball 148 which normally rests loosely on a seat 152 at the bottom of chamber portionn 146a. The top wall 144a of the housing has a passage 154 which opens to the atmosphere. Also, the underside of wall 144a around passage 154 is recessed at 156 and an O-ring 158 is positioned in the recess so that when ball 148 is moved up against the ring, a seal is formed between those elements, thereby closing off passage 154.

Normally, ball 148 rests on seat 152 as shown in dotted lines in FIG. 1. Any gas that enters passage 142 flows up into chamber 146. Thus, gas is able to pass up around ball 148 lifting the ball slightly as needed and escape through passage 154 at the top of the housing. Preferably, baffles 159 are provided between passage 142 and chamber 146 to prevent the ball 148 from being driven up against the O-ring 158 by fluid jetting into chamber 146.

When liquid refrigerant is conducted into the passage 142, it flows up into chamber 146 and lifts ball 148 so that it seats against the O-ring. This closes passage 154 so that the liquid cannot escape from the valve. Thus, only liquid refrigerant flows out of passage 142 into pipe 49. This assures that only liquid refrigerant flows to probe 18 during the freeze mode so that its tip 18a is cooled to a maximum extent.

The liquid refrigerant flows via hose passage 16a through the small diameter feed tube 94 to the probe tip 18a. The end 94a of the tube inside housing 88 is slightly flared to prevent the formation of solid refrigerant at that point which might obstruct the end of the tube and interfere with the flow of refrigerant. The refrigerant issuing from tube 94 bathes the working surface 88a of the probe tip. It cools the surface through evaporation [of] *to* a very low temperature on the order of −88°C very quickly, i.e., 2–5 seconds, so that any tissue contacted by that surface freezes rapidly.

After issuing from tube 94 and cooling surface 88a, the refrigerant is now heated to the point where it is substantially in a gaseous state. Thereupon, it follows two separate avenues of escape from the tip. Most of the gas flows through the relatively large diameter exhaust tube 96 and is thence conducted by the hose passage 16b through the heat exchanger 54 and thence to the atmosphere through the muffler 46 at valve 36. Since the heat exchanger is maintained at a constant temperature, e.g., +50°C, the gas vented to the atmosphere is not excessively cold. During this time, of course, the thermostatic switch 62 responds to the relatively cold gas flowing through tube 44 by cycling the heater 56 on and off to maintain the selected constant temperature.

The other avenue of escape of gas from the probe tip is through the bleed tube 98. The gas escaping through tube 98 is conducted via hose passage 16c to the coupling passage 50c where it vents to the atmosphere.

It should be mentioned at this point that while the housing 88 at the probe tip is maintained at a very low temperature during the freeze cycle and the sleeves 76 and 84 are also quite cold, the insulating jacket formed by the plastic handle 72 and barrel extension 82 prevents these cold surfaces of the probe from inadvertently contacting tissue adjacent the area being operated on and enables the operator to hold the probe comfortably for a relatively long period of time.

When the operator releases the foot switch 15, the flow of refrigerant through the system reverses, as shown by the dotted lines in FIG. 1. Thus, refrigerant is conducted by way of valve 36 to the heat exchanger where it is heated on the order of 25°–50°C. The heated fluid is then conducted via hose 16b to the probe tip where it heats the surface 88a to a sufficiently high temperature to thaw the contacted tissue. This occurs very quickly, i.e., on the order of 5–10 seconds. The rapid defrost cycle is due to the fact that there is a relatively high rate of flow of heated fluid to the probe tip where it gives up heat at the surface 88a. Pressure of the fluid in the tip housing is maintained at a level above the saturation pressure corresponding to 0°C for the particular working fluid by introducing the heated fluid under pressure through a large inlet tube 96 and exhausting the fluid from the housing to the atmosphere through both tubes 94 and 98 which restrict flow to a great degree.

The apparatus operates in the defrost mode until it is turned off automatically after a selected period of time by timing circuit 132 whereupon all flow of refrigerant ceases. As mentioned previously, if the system remains in this ready condition long enough to allow gas to form in valve 34 and line 38, this is purged from the system through valve 48 when the operator next depresses the foot switch 15 to commence another freeze cycle.

As seen from the foregoing then, the present apparatus maintains close control over the probe tip temperature during both the freeze and defrost modes of operation without requiring any special heat-sensing devices or heaters in the probe itself. This simplifies the construction of the probe and reduces the incidence of probe failures to as close to zero as possible. Also, the lack of electrical elements in the probe and complete electrical isolation of the probe eliminate any hazard of a spark from the probe igniting flammable vapors in the vicinity of the patient, and eliminate any electrical paths between patient, probe and other electrical equipment which may be attached to the patient.

Also, since a high flow rate of liquid refrigerant with super cooling power is achieved at the probe tip, the tip can be brought to a very low temperature in a very short time. On the other hand, the utilization of the back pressure defrost feature by which the refrigerant is passed through a heater prior to being conducted to the probe tip enables the probe to be quickly detached from the tissue contacted by it. Yet, with all of these advantages, the present cryosurgical apparatus is simple to make and to operate. Also, its initial and maintenance costs are relatively low.

As will be seen from the foregoing, the objects set forth above, among those made apparent by the preceding description, are efficiently attained and, since certain changes may be made in the above construction without departing from the scope of the invention, it is intended that all matter contained in the above description or shown in the accompanying drawings, shall be interpreted as illustrative and not in a limiting sense.

It is also to be understood that the following claims are intended to cover all of the generic and specific features of the invention herein described.

We claim:

1. Cryosurgical apparatus comprising

A. a probe having a hollow probe tip,

B. a first tube extending to a point inside the probe tip,

C. a second tube extending to a point inside the probe tip, *said second tube being sufficiently less restrictive than the first tube that when fluid is supplied to the tip through the first tube sufficient exhaust will pass through the second tube to cool the tip below 0°C,*

D. means for conducting a fluid refrigerant to the first tube so that it flows into the probe tip and exhausts therefrom through the second tube thereby rapidly cooling the tip [,] *to a first temperature sufficiennt to freeze human tissue, and*

E. *second* means for conducting [the] refrigerant [to the second] *at a temperature higher than said first temperature* [tube so that it flows] to the probe tip through the second tube [and] *so that it* exhausts therefrom through the first tube, [and] *thereby warming the tip.*

[F. means adjacent the second conducting means for heating the refrigerant prior to its introduction into the second tube so that the fluid entering the probe tip through the second tube and exhausting therefrom through the first tube rapidly heats the probe tip.]

2. Cryosurgical apparatus defined in claim 1 further including a source of liquid refrigerant for connection alternately to the first and second conducting means so that the refrigerant is conducted to the [proe] *probe* tip through the first tube as an unheated liquid and is conducted to the probe tip through the second tube [ after being heated by the heating means ] as a relatively warm fluid.

3. Cryosurgical apparatus as defined in claim 2 and further including means connected to said first conducting means for purging the first conducting means of gas without permitting appreciable leakage of fluid.

4. Cryosurgical apparatus as defined in claim 3 wherein said purging means is comprised of A. a housing extending [ up ] from the conducting means and communicating therewith, B. a vent passage [ (at the top of) ] in the housing, and C. a *bouyant* valve member movable within the housing, said valve member 1. being urged [ by gravity ] toward the [ (bottom of the chamber,) ] housing wall opposite the vent passage, 2. being [ (lifted) ] shifted toward the vent passage only slightly in response to gas entering the housing from the first conducting means so as to allow passage thereof of the vent passage, and 3. being [ moved (up) ] *floated* againt the [ (top of the housing) ] vent passage when liquid enters the housing from the first conducting means so as to block the vent passage.

5. Cryosurgical apparatus as defined in claim 2 wherein the refrigerant source contains liquid nitrous oxide.

6. Cryosurgical apparatus as defined in claim 1 *and including* [ wherein the heating means include ] means for maintaining the refrigerant flowing through the second conducting means at a substantially constant temperature above 0°C.

7. Cryosurgical apparatus as defined in claim 1 and further including a *two-ended* third tube inside the probe, said third tube having its one end communicating with the inside of the probe tip and its other end venting to the atmosphere, said third tube conducting fluid inside the probe tip [ of ] *to* atmosphere.

8. Cryosurgical apparatus as defined in claim 7 wherein

A. the first tube has a first internal diameter, and

B. the second tube has a second larger internal diameter.

9. Cryosurgical apparatus as deffined in claim 8 wherein the internal diameter of the third tube is smaller than that of the first tube.

10. Cryosurgical apparatus as defined in claim 1 *and including* [ wherein the ] heating means [ is ] comprised of A. a heater in intimate thermal exchange relation with the second conducting means so that the conducting means and any fluid flowing therein is heated by the heater, and B. a temperature responsive switch for controlling the energizing of the heater so as to maintain the [ hpater ] *heater* at a substantially constant temperature.

11. Cryosurgical apparatus as defined in claim 1

A. wherein the first and second conducting means include first and second three-way solenoid valves, respectively, each said valve having 1. a first port leading to only one of said tubes in the probe, 2. a second port for connection ot a refrigerant source, and 3. a third port venting to the atmosphere, and B. means for operating the two valves out of phase with each other so that 1. when the first tube is connected to receive refrigerant through the first valve, said second tube is connected to exhaust to the atmosphere through the second valve, and 2. when the second tube is connected to receive refrigerant through the second valve, the first tube is connected to exhaust to the atmosphere through the first valve.

12. Cryosurgical apparatus as defined in claim 11 wherein the actuating means includes timing means for controlling the length of time the three-way valves are in at least one of their two operative positions.

13. Cryosurgical apparatus comprising

A. a probe having 1. a hollow tip, 2. a first small diameter tube extending through the probe and terminating at a point inside the tip, 3. a second small diameter tube extending through the probe and terminating at a point inside the tip, and 4. a third tube extending through the probe and communicating with the interior of the probe tip, B. means for supplying refrigerant to the first tube so that the refrigerant flows to the probe tip and exhausts through both the second and third tubes, thereby rapidly cooling the probe tip, and C. means for conducting any refrigerant exhausting from the tip through the second and third tubes away from the probe.

14. Cryosurgical apparatus as defined in claim 13 wherein the third tube is smaller in internal diameter than the first tube and the second tube is larger in internal diameter than the first tube.

15. Cryosurgical apparatus as defined in claim 14 wherein the first tube is 0.028 inch in diameter, the second tube is 0.064 inch in diameter and the third tube is similar [ to ] *in* bore size to the first tube.

16. Cryosurgical apparatus as defined in claim 13 and further including means for conducting a relatively warm fluid into the probe tip through the second tube and exhausting it from the tip through the first and third tubes, thereby rapidly warming the tip.

17. Cryosurgical apparatus as defined in claim 16 wherein the warm fluid conducting means includes A. a conduct for supplying refrigerant to the second tube, B. means for heating the conduit, and C. means for controlling the heating means so as to maintain the conduit at a selected temperature.

18. Cryosurgical apparatus as defined in claim 16 wherein the bore size of the second tube is larger than the combined bore sizes of the first and third tubes so that in the defrost mode, the fluid conducted to the tip through the second tube is maintained at a pressure inside the tip greater than the saturation pressure corresponding to 0°C for the particular working fluid being circulated.

*19. Cryosurgical apparatus comprising*

*A. a probe having a hollow thermally conductive tip,*

*B. a single fluid refrigerant path extending through the tip, said path having a relatively restrictive part communicating with the interior of the tip and a less restrictive part communicating with the interior of the tip,*

*C. means for flowing refrigerant at a selected temperature above 0°C along said path so that the refrigeran*

*flows along the more restrictive part of the path into the tip and exhausts from the tip along the less restrictive part of the path so that the refrigerant cools the tip to a first temperature sufficiently low to freeze human tissue, and*

*D. means for subsequently reversing flow of refrigerant so that the refrigerant flows along the less restrictive part of the path into the tip and exhausts from the tip along the more restrictive part of the path so that the refrigerant warms the tip to a second temperature above 0°C.*

*20. Cryosurgical apparatus comprising:*

*A. a probe having a hollow probe tip,*

*B. a first tube in communication with the inside of the probe tip,*

*C. a second tube in communication with the inside of the probe tip, said first tube being more restricted than said second tube,*

*D. means for conducting a fluid refrigerant at an initial temperature above 0°C through the first tube into the probe tip so that it exhausts therefrom through the second tube whereby the refrigerant temperature inside the tip drops substantially below 0°C, thereby cooling the tip, and*

*E. means for reversing the direction of refrigerant flow at the initial temperature through the probe tip so that said refrigerant is conducted through the second tube into the probe tip and exhausts therefrom through the first tube whereby the refrigerant temperature inside the tip is above 0°C so that the refrigerant warms the tip.*

*21. Cryosurgical apparatus as defined in claim 20, wherein*

*A. the first and second conducting means include first and second three-way solenoid valves, each said valve having*

*1. a first port leading to only one of said tubes in the probe,*

*2. a second port for connection to a refrigerant fluid source, and*

*3. a third port venting to the atmosphere, and*

*B. the reversing means comprise means for operating the two valves out of phase with each other so that*

*1. when the first tube is connected to receive refrigerant through the first valve, said second tube is connected to exhaust to the atmosphere through the second valve, and*

*2. when the second tube is connected to receive refrigerant through the second valve, the first tube is connected to exhaust to the atmosphere through the first valve.*

*22. Cryosurgical apparatus comprising*

*A. a fluid refrigerant probe having a hollow tip,*

*B. a first tube in communication with the inside of the tip,*

*C. a second tube in communication with the inside of the tip,*

*1. said second tube being sufficiently less restrictive than the first tube that when fluid is supplied to the tip through the first tube, sufficient exhaust will pass through the second tube to cool the tip below 0°C, and*

*2. said first tube being sufficiently more restrictive than the second tube so that when fluid is supplied to the tip through the second tube and exhausts therefrom through the first tube, the pressure in the tip exceeds the pressure when fluid refrigerant exists as saturated vapor in equilibrium with its liquid at 0°C so that the tip is warmed above 0°C,*

*D. means for flowing refrigerant through the first tube to the inside of the tip so that it exhausts from the second tube, and*

*E. means for reversing the direction of refrigerant flow through the tip so that the refrigerant is supplied to the second tube and exhausts from the first tube.*

* * * * *